(12) United States Patent
Licht

(10) Patent No.: US 10,966,502 B2
(45) Date of Patent: Apr. 6, 2021

(54) SWAB ROLLER

(71) Applicant: BIA-America, LLC, Saratoga, CA (US)

(72) Inventor: Bridget Licht, Sunnyvale, CA (US)

(73) Assignee: BIA-America, LLC, Saratoga, CA (US)

( * ) Notice: Subject to any disclaimer, the term of this patent is extended or adjusted under 35 U.S.C. 154(b) by 401 days.

(21) Appl. No.: 16/123,229

(22) Filed: Sep. 6, 2018

(65) Prior Publication Data

US 2019/0069663 A1  Mar. 7, 2019

Related U.S. Application Data

(60) Provisional application No. 62/554,568, filed on Sep. 6, 2017.

(51) Int. Cl.
*A61F 13/38* (2006.01)
*A45D 34/04* (2006.01)

(52) U.S. Cl.
CPC ............ *A45D 34/041* (2013.01); *A61F 13/38* (2013.01); *A45D 2200/1018* (2013.01)

(58) Field of Classification Search
CPC ........ A61F 11/006; A61F 13/36; A61F 13/38; A45D 34/04–043; A45D 2200/10–1018
See application file for complete search history.

(56) References Cited

U.S. PATENT DOCUMENTS

| | | | | |
|---|---|---|---|---|
| 977,825 | A * | 12/1910 | Murphy | A61B 17/00234 604/1 |
| 4,136,680 | A * | 1/1979 | Southworth | A61B 10/02 435/304.1 |
| 5,334,212 | A * | 8/1994 | Karell | A61B 1/227 128/864 |
| 6,245,037 | B1 * | 6/2001 | Reum | B05C 17/02 15/230.11 |
| 2003/0201199 | A1 * | 10/2003 | Bennett | A61F 13/38 206/361 |
| 2012/0260931 | A1 | 10/2012 | Martin et al. | |
| 2013/0056020 | A1 * | 3/2013 | Wilson | B05C 17/00 132/320 |

(Continued)

FOREIGN PATENT DOCUMENTS

CN 2928060 Y 8/2007
CN 202740621 U 2/2013
(Continued)

OTHER PUBLICATIONS

Machine Translation of FR-2830432-B3 (Year: 2003).*
Machine Translation of DE 196 10 998 A1 (Year: 1997).*

*Primary Examiner* — Benjamin J Klein
(74) *Attorney, Agent, or Firm* — McHale & Slavin, P.A.

(57) ABSTRACT

A swab roller formed from an elongated stem having a first end terminating with a covering and a second end terminating with a covering. A casing tube placed over a portion of the elongated stem is sized to allow the rotation of the elongated stem within the casing tube. The covering is formed from an absorbent material such as cotton or foam. The swab roller can be constructed of inexpensive components, such as paper for general use or from medical grade materials or sterile packaging for specialty use.

13 Claims, 2 Drawing Sheets

(56) References Cited

U.S. PATENT DOCUMENTS

| | | | | |
|---|---|---|---|---|
| 2015/0291779 A1* | 10/2015 | Hani | ...................... | A23G 9/503 |
| | | | | 426/134 |
| 2016/0166268 A1* | 6/2016 | Toppins | ................ | A61B 17/50 |
| | | | | 606/162 |
| 2016/0310154 A1* | 10/2016 | Harkless | ............... | A61F 13/126 |

FOREIGN PATENT DOCUMENTS

| | | | | |
|---|---|---|---|---|
| CN | 203989448 U | 12/2014 | | |
| CN | 204594716 U | 8/2015 | | |
| CN | 105362062 A | 3/2016 | | |
| CN | 205434676 U | 8/2016 | | |
| CN | 106925541 A | 7/2017 | | |
| CN | 206366094 U | 8/2017 | | |
| CN | 206372389 U | 8/2017 | | |
| DE | 196 10 998 A1 * | 9/1997 | | |
| FR | 2830432 B3 * | 11/2003 | ............ | A61F 13/38 |
| GB | 2 380 122 * | 4/2003 | | |
| JP | 2014128447 A | 7/2014 | | |
| WO | WO2017059198 | 4/2017 | | |

* cited by examiner

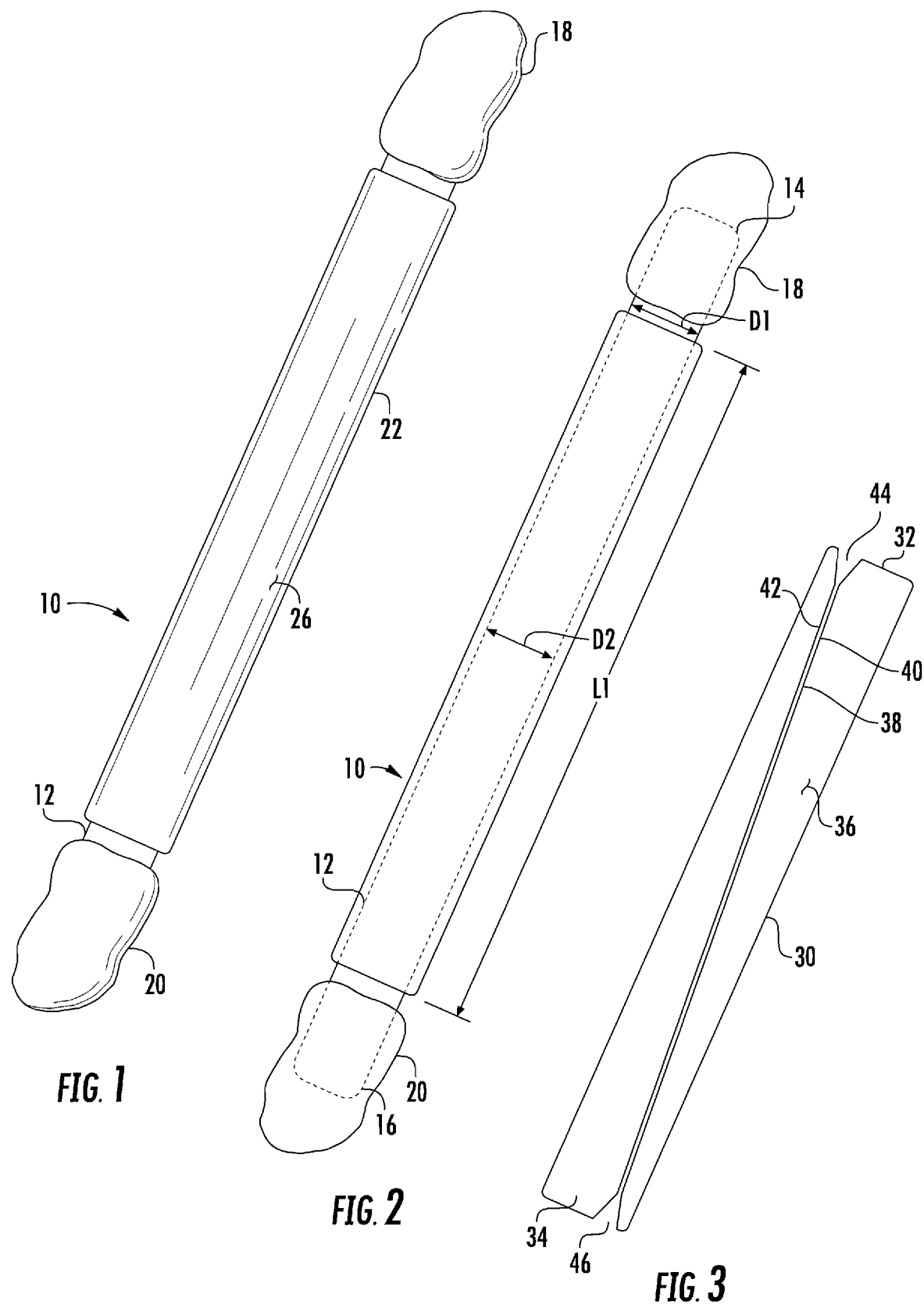

SWAB ROLLER

PRIORITY CLAIM

This invention is based upon and claims the priority date of U.S. Provisional Patent Application 62/554,568 filed Sep. 6, 2017, and entitled "COTTON/FOAM ROLLER", the contents of which are incorporated herein by reference.

FIELD OF THE INVENTION

The invention relates to swabs and, in particular, to a rotatable swab useful in cosmetic and wound dressing applications.

BACKGROUND OF THE INVENTION

Swabs are well known in the industry for use in cleaning. A conventional swab employs an absorbent covering located on either end of an elongated stem. The absorbent material can be made from a variety of materials, with cotton likely the most well-known. The elongated stem may be made of paper, plastic or similar material having stiff or bendable properties. The absorbent material may be attached by an adhesive or with frictional engagement. A problem with the conventional swab is that the absorbent material is held in a fixed position, wherein the swab can be abrasive when drawn across a sensitive member.

For instance, in cosmetics, the drawing of a swab across the skin may operate to remove matter from the skin. In many instances, the use of the swab would be beneficial in applying various types of cosmetics, in essence avoiding removal of applied cosmetics. This may be accomplished by dabbing the swab across the skin, or causing the absorbent material to roll across the skin by spinning the elongated stem between the applicant's fingers. This can be a difficult task to master, especially if the applicant does not have good dexterity.

A more pointed example may be found in the medical field, wherein the drawing of a swab across the skin may cause irritation. In many instances, the usefulness of the swab would greatly increase if the swab was rotated across the skin, wherein the absorbent material would operate as an applicator. Surgical incisions, skin burns, and other tissue wounds must be carefully treated to prevent infection. Surgical incisions must also be dressed periodically to facilitate healing. Tissue wounds may be dressed using sterile saline, iodine, peroxide or the like disinfectant. The use of a swab applicator facilitates the process by providing a single use applicator that can be dipped into a disinfectant before use. Medical use is not limited to surgical incisions; most every type of skin issue would benefit from a single use applicator that applies ointments without the fear of dragging or otherwise irritating the skin. For instance, skin issues such as dermatitis, eczema, impetigo, psoriasis, rosacea and so forth would benefit from a single use applicator of ointment that does not require the applicator to have special skills. When the applicator is wiped or dragged directly over the wound to apply the disinfectant or ointment, not only can the applicator cause skin irritation, it can spread infection from one area to another. If the applicator is rolled over the wound, the motion avoids the transfer of the infection from one portion of the wound to the other. This requires the applicator to match the surface speed of the absorbent material to that of the swab movement. However, conventional swab heads are typically small in circumference and fixed to the handle of the device. A person can manually rotate the elongated stem and cause the swab to rotate as well, but the dexterity required to match the surface speed of the head to that of the handle is difficult and can be cumbersome.

While the above-mentioned use of applicators can be accomplished by rotating the elongated stem between the fingers during use, the rotation requires a certain amount of dexterity. In many instances, the individual may not have the dexterity or patience, or may be wearing gloves, making rotation of the elongated stem between the fingers difficult, if not impossible, to perform.

Prior art attempts to make a rotating applicator are complicated and expensive. U.S. Patent Publication 2012/0260931 discloses a cosmetic handheld applicator assembly. The applicator assembly system employs a handle, a motor, and a coupling assembly for releasably receiving a set of detachable and interchangeable makeup brushes selected for applying a cosmetic to a surface area of the body zones.

WO2017059198A1 discloses a makeup brush which has a generally cylindrical body having a first end adapted to be rotatably coupled to a motorized makeup brush support, a second end defining a recess therein that is adapted to receive a plurality of bristles, and a central axis that extends between the first end and the second end.

CN2928060Y discloses an electric therapeutic otitis curer, which comprises a shell and a cotton bar. A direct current supply and a direct current motor are arranged on a shell. A cotton bar is arranged on the front of the shell and is connected to the motor through a drive shaft.

CN202740621U discloses a partial sterilizer having a handle, storage battery and a motor. The partial sterilizer is characterized in that a rotating head is arranged at the front end of the handle, and a cotton ball clamp is arranged on the rotating head.

CN203989448U discloses a rolling applicator having a universal joint arranged at the top end of a handle and matched with a ball socket and a ball.

CN205434676U discloses a medical care cotton swab auxiliary device. The device includes a cylinder branch. A right hand member of the cylinder branch is provided with a handle, and the left side of the cylinder branch is provided with a dwang; the near-end of the dwang and cylinder branch is connected through a damping pivot. The left end of the dwang is provided with a connection socket, and the left end surface middle part is provided with the blind hole. The blind hole inner circle is provided with the elastic gum ring. The elastic gum with intra-annular pegged graft holds a cotton swab.

CN105362062A discloses a nasal cleaner using a water spray type cotton swap as a cleaning head, and an infusion tube with an infusion bottle connected with each other to form the water spray washing and scrubbing linkage type nasal cleaner.

CN204594716U discloses a swab that can prevent rotary droing. It comprises a locking cap, swab, and external packing union coupling, with three recesses in a rigid plastic locking cap. The anti-removal swab connection package has a center shaft that is set with the cap and groove, such that swab end is set with a rib by a clamping connection.

CN206366094U discloses a portable medical cotton stick, including a cavity handle with a cotton stick on one end and a source of iodophor at the other end. The iodophor passes through a threaded connection between the cavity handle.

CN206372389U discloses a disinfection cotton swab having a main part forming a cavity plastic tubing, a middle part of cavity plastic tubing being an air chamber with both upper and lower ends having an iodophor cavity and an alcohol cavity.

JP2014128447A discloses a cosmetic tool for applying an adhering cosmetic onto a skin uniformly. The applicator includes a rotating application part having an implanted brush.

What is needed in the industry is a disposable rolling swab applicator that is inexpensive to manufacture and is not dependent upon an individual's dexterity for operation.

SUMMARY OF THE INVENTION

A swab roller formed from an elongated stem having a first end terminating with a covering and a second end terminating with a covering is disclosed. A casing tube is placed over a portion of the elongated stem, which is sized to allow the rotation of the elongated stem within the casing tube. In a preferred embodiment, the covering is formed from an absorbent material, such as cotton or foam. The swab roller can be constructed of inexpensive components, such as paper, for general use, or from medical grade materials or sterile packaging for specialty use.

An objective of the invention is to provide an inexpensive swab roller having a particular use for cosmetic or medical usage.

Another objective of the invention is to provide a swab roller device that can be used by an individual wearing gloves or otherwise has limited dexterity.

Still another objective of the invention is to provide a casing tube for adapting to a conventional swab to allow ease of rolling the swab.

Another objective of the invention is to provide a swab roller having at least one covering formed from an absorbent material such as cotton, foam, nylon or polyester, and an elongated stem formed from either paper or plastic.

Yet still another objective of the invention is to provide a swab roller construction using tips having a leading edge and a trailing edge with ridges therebetween, wherein the ridges allow unidirectional insertion into an adjoining stem.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE DRAWINGS

FIG. 1 is a perspective view of the swab roller;
FIG. 2 is FIG. 1 with hidden lines;
FIG. 3 is a plane view of a casing tube.

DETAILED DESCRIPTION OF THE PREFERRED EMBODIMENT

Figure 4:
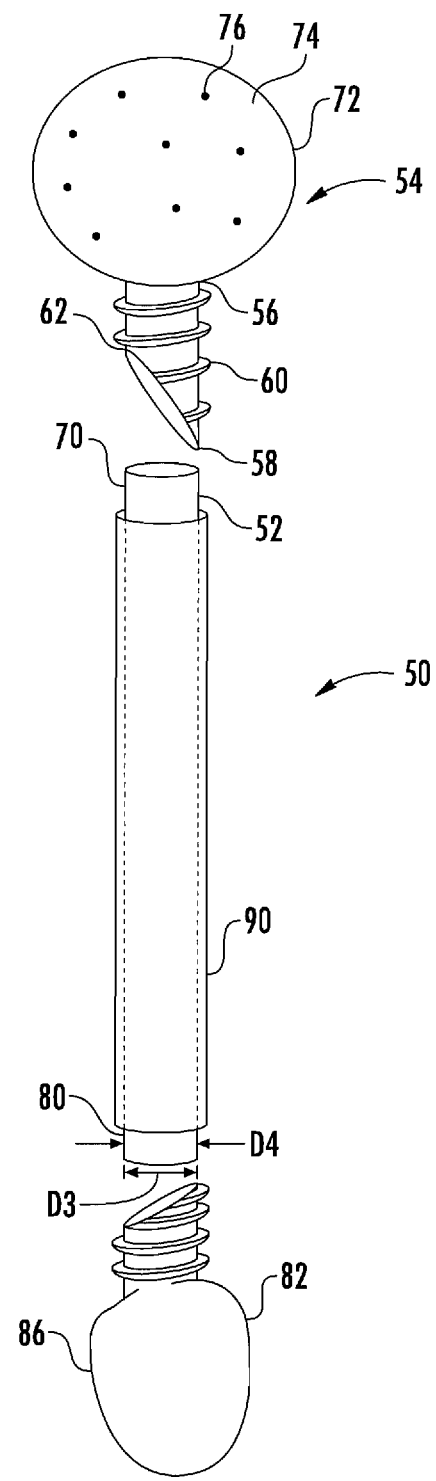
FIG. 4 is an exploded view of an alternative embodiment of the swab roller.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Referring to FIGS. 1 and 2, illustrated is the swab roller 10 of the instant invention. The swab roller 10 is constructed of an elongated stem 12, which is further defined by a first end 14 spaced apart from a second end 16. The stem 12 is made of either rolled paper or plastic with an outer diameter D1 of about 3 mm. A covering 18 is secured along the first end 14 by either adhesive or frictional engagement. If the covering is made of cotton or the like absorbent, securement is preferably by adhesive. If the covering is made of foam or the like material, securement can be by frictional engagement, wherein the covering can be forced on or adherence is obtained by use of heat, causing the covering and the stem to fuse together.

A casing tube 22 is positioned between the first end 14 and the second end 16, preferably during the assembly stage. In this embodiment, the casing tube 22 is placed over the elongated stem 12 before the first or second covering 18, 20 is secured to the first or second end 14, 16. The casing tube 22 has a horizontal length L1 that fits over a portion of the stem 12, and a continuous sidewall 26. The casing tube 22 is constructed of thin wall paper or plastic having a thickness of about 0.1 mm to 0.5 mm. Thin wall paper can be made of helically wound plies of paper which are treated to be substantially impervious to fluid. Treated thin wall paper provides an inner surface having a lower coefficient of friction, over untreated paper to allow ease of rotation of the stem 12 within the casing tube 22. In one embodiment, the stem 12 is paper and the casing tube 22 is formed of treated paper, providing a most cost effective rolling swab that is environmentally friendly.

Another embodiment employs a paper stem 12 and a plastic casing tube 22. The use of a plastic casing tube 22 allows for ease of stem rotation due to the inherent low coefficention of friction of a smooth casing tube 22 formed of plastic. Similar to the previously mentioned paper casing tube, placement of the plastic casing tube in position during the assembly stage allows ease of attachment when either the first covering 18 or second covering 20 has yet to be secured.

In an alternative embodiment, a casing tube 30 is attached to a conventional swab after assembly. In this embodiment, a first and second covering is attached to an elongated stem, and the casing tube 30 is pushed over the elongated stem. As illustrated in FIG. 3, a push on casing tube 30 is formed of thin wall plastic having a first end 32 and a second end 34. In this embodiment, the sidewall 36 is not continuous and includes a first edge 38 spaced apart from a second edge 42, forming a slit 40 therebetween. To allow ease of installation, a first V-shaped notch 44 is positioned along the first end 32 and a second V-shaped notch 46 is positioned along the second end 46. The V-shaped notch assists in installation, wherein the notch is placed against the stem which results in the slit 40 being made large enough to side over the outer diameter of the stem. The plastic casing tube 30 maintains a memory, wherein the casing tube 30 captures the stem and returns to an original diameter. The slit 40 formed by the space between the ends 38 and 42 of the tube 30 is preferably placed at an angle to allow ease of stem rotation without the edges 38, 42 engaging the stem.

Referring now to FIG. 4, set forth is another embodiment of the roller swab 50 having an elongated stem 52 having an inner diameter D3 and an outer diameter D4. In this embodiment, a first end 54 is constructed from an insertion tip 56 having a leading edge 58 with a series of directional barbs 60 spaced apart along the outer surface 62 of the insertion tip

56. The insertion tip 56 is driven into the first end 70 of the stem 52. The directional barbs 60 allow a one way insertion of the insertion tip 56 into the stem 52. Alternatively, the insertion tip 56 can be attached to the stem 52 by adhesive or fused together using heat. A covering 72 is attached to the insertion tip 56 in the same manner as previously described. The covering 72 depicted illustrates a variation using material with absorption properties 74 and material with non-absorption properties 76?.

A second end 80 for receipt of a second insertion end 82 operates in the same manner as the first insertion end 54. In this illustration, a foam covering 86 is placed over the insertion tip 82. Casing tube 90 is positioned over a portion of the stem 52, allowing the stem and insertion tips to freely rotate.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A swab roller comprising:
    an elongated stem having an outer diameter with a first end and a second end;
    a casing tube having an inner diameter constructed and arranged to fit over a portion of said elongated stem;
    a first covering securable to said first end; and
    a second covering securable to said second end; wherein said elongated stem can rotate within said casing tube, allowing said first and second covering to roll over a surface while said casing tube is held in a fixed position relative to said elongated stem.

2. The swab roller according to claim 1 wherein at least one covering is formed from an absorbent material.

3. The swab roller according to claim 2 wherein said absorbent material is selected from the group consisting of cotton, foam, nylon and polyester.

4. The swab roller according to claim 1 wherein at least one covering is a mixed cover formed from an absorbent material interspaced with a non-absorbent material.

5. The swab roller according to claim 1 wherein said elongated stem is selected from the group consisting of paper or plastic.

6. The swab roller according to claim 1 wherein said casing tube is constructed from a hollow plastic tube having a continuous sidewall.

7. The swab roller according to claim 1 wherein said casing tube is constructed from a hollow plastic tube having a slit extending from a first end to a second end, said slit providing a space for placement around said elongated stem.

8. The swab roller according to claim 7 including a first V-shaped notch extending from said first end to said slit, and a second V-shaped notch extending from said second end to said slit.

9. The swab roller according to claim 1 wherein each said covering is further defined as a tip having a proximal end securable to said elongated stem and a distal end having said covering.

10. The swab roller according to claim 9 wherein said proximal end is tubular shaped having a leading edge and a trailing edge with ridges therebetween, wherein said proximal end ridges allowing unidirectional insertion into said elongated stem.

11. The swab roller according to claim 1 wherein said casing tube includes a length with a slit extending the length of said casing tube, wherein said slit allows placement of said casing tube over said elongated stem.

12. The swab roller according to claim 1 wherein said first covering is formed from the same material as said second covering.

13. The swab roller according to claim 1 wherein said elongated stem and said casing tube are constructed from medical grade plastic.

\* \* \* \* \*